(12) United States Patent
White

(10) Patent No.: US 11,752,448 B1
(45) Date of Patent: Sep. 12, 2023

(54) DEVICE AND METHOD FOR VACUUM DISTILLING CANNABIS TERPENES

(71) Applicant: Ken Jahn White, Terrebonne, OR (US)

(72) Inventor: Ken Jahn White, Terrebonne, OR (US)

(*) Notice: Subject to any disclaimer, the term of this patent is extended or adjusted under 35 U.S.C. 154(b) by 0 days.

(21) Appl. No.: 17/731,133

(22) Filed: Apr. 27, 2022

Related U.S. Application Data

(60) Provisional application No. 63/161,222, filed on Mar. 15, 2021.

(51) Int. Cl.
*B01D 3/10* (2006.01)
*B01F 27/722* (2022.01)
*B01D 8/00* (2006.01)

(52) U.S. Cl.
CPC ............... *B01D 3/10* (2013.01); *B01D 8/00* (2013.01); *B01F 27/722* (2022.01)

(58) Field of Classification Search
CPC ............ B01D 3/10; B01D 8/00; B01F 27/722
See application file for complete search history.

(56) References Cited

U.S. PATENT DOCUMENTS

| | | | | |
|---|---|---|---|---|
| 5,183,540 A * | 2/1993 | Rubin | ............... | B01D 3/10 202/205 |
| 5,409,541 A * | 4/1995 | Walker | ............... | A23N 1/00 127/2 |
| 9,034,395 B2 * | 5/2015 | Whittle | ............... | B01D 11/0288 424/494 |
| 10,478,747 B2 * | 11/2019 | Ko | ............... | C11B 1/108 |
| 10,618,025 B2 * | 4/2020 | Ostvik | ............... | C10J 3/74 |
| 10,646,793 B2 * | 5/2020 | Ko | ............... | C11B 3/12 |
| 11,124,725 B2 * | 9/2021 | Ostvik | ............... | B01J 19/0066 |
| 2010/0261895 A1 * | 10/2010 | Noll | ............... | C12M 21/04 422/118 |
| 2019/0143246 A1 * | 5/2019 | Ko | ............... | B01D 15/00 422/270 |
| 2019/0308159 A1 * | 10/2019 | Ostvik | ............... | B01J 19/20 |
| 2022/0178611 A1 * | 6/2022 | Bonefas | ............... | B01F 27/70 |

FOREIGN PATENT DOCUMENTS

CN 112569622 A * 3/2021 ............... B01D 3/10

* cited by examiner

*Primary Examiner* — Jonathan Miller
(74) *Attorney, Agent, or Firm* — Plager Schack LLP; Mark H. Plager; Kara Verryt

(57) ABSTRACT

A system for vacuum distilling terpenes from plant material, such as from cannabis, may include an extractor having an extractor body with a lower discharge manway, a top loading manway, an interior chamber with an agitator rotatable mounted within the interior chamber, and a dimple jacket encircling at least a portion of an exterior of the extractor body; a cold trap operatively attached to the extractor body, such that volatilized terpenes travel from the extraction body to the cold trap to condense/freeze; a circulating fluid chiller operatively attached to the cold trap; a heated fluid circulator operatively attached to the dimple jacket; a vacuum operatively attached to the extractor body, such that the vacuum is capable of reducing pressure within the extractor body; and a heat exchanger operatively attached to the heated and chilled fluid circulators and the extractor body.

10 Claims, 6 Drawing Sheets

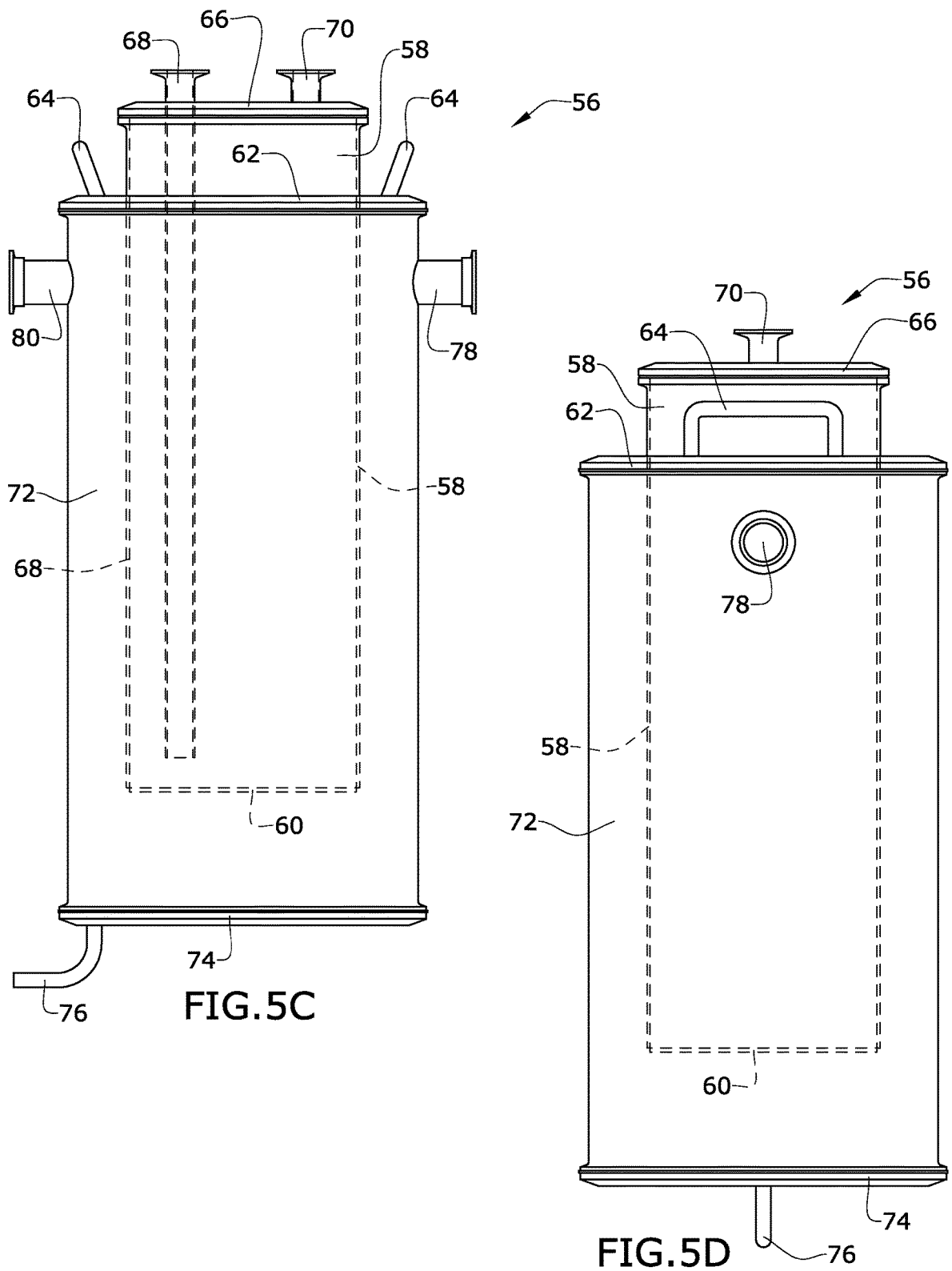

DEVICE AND METHOD FOR VACUUM DISTILLING CANNABIS TERPENES

RELATED APPLICATION

This application claims priority to provisional patent application U.S. Ser. No. 63/161,222 filed on Mar. 15, 2021, the entire contents of which is herein incorporated by reference.

BACKGROUND

The embodiments described herein relate generally to cannabis terpene isolation and, more particularly, to a device and method for vacuum distilling cannabis terpenes.

Conventional methods for cannabis terpene isolation include primarily steam distillation, co-extract flavonoid, and other undesirable polar phytochemicals. The intense thermal energy utilized in steam extraction also leads to cannabinoid degradation, as well as degradation and polymerization of present terpenes, thereby producing foul odors and ultimately low quality product. Existing methods also saturate plant biomass with water, requiring post process drying.

Therefore, what is needed is a method and device for vacuum distillation of cannabis terpenes that is solventless and utilizes gentle heat and strong vacuum to reduce boiling points of temperature sensitive terpene compounds.

SUMMARY

Some embodiments of the present disclosure include a system for vacuum distilling terpenes from plant material, such as from cannabis. The system may include an extractor having an extractor body with a lower discharge manway, a top loading manway, an interior chamber with an agitator rotatable mounted within the interior chamber, and a dimple jacket encircling at least a portion of an exterior of the extractor body; a cold trap operatively attached to the extractor body, such that volatilized terpenes travel from the extraction body to the cold trap to condense/freeze; a circulating fluid chiller operatively attached to the cold trap; a heated fluid circulator operatively attached to the dimple jacket; a vacuum operatively attached to the extractor body, such that the vacuum is capable of reducing pressure within the extractor body; and a heat exchanger operatively attached to the heated and chilled fluid circulators and the extractor body.

BRIEF DESCRIPTION OF THE FIGURES

The detailed description of some embodiments of the invention is made below with reference to the accompanying figures, wherein like numerals represent corresponding parts of the figures.

FIG. 5C is a font view of cold trap 56 from one embodiment of the present disclosure.

FIG. 5D is a right side view of cold trap 56 from one embodiment of the present disclosure.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to vacuum distill cannabis terpenes and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

The various elements of the present disclosure may be related in the following exemplary fashion. It is not intended to limit the scope or nature of the relationships between the various elements, and the following examples are presented as illustrative examples only.

By way of example, and referring to FIGS. 1-6, some embodiments of the present disclosure include a method and system for vacuum distillation of cannabis terpenes, wherein the process is solventless and utilizes gentle heat and strong vacuum to reduce the boiling points of temperature sensitive terpene compounds. During the method of the present disclosure, terpenes are isolate in precise ratios found in the utilized plant material. Extraction occurs in an oxygen free environment and, thus, no degradation of terpenes or cannabinoids occurs, resulting in a high quality and highly pure terpene extract suitable for many applications. The process plant material is stripped and terpenes and residual water content while retaining full cannabinoid content. Removal of the residual water content in the plant material during the method of the present disclosure improves downstream cannabinoid extraction.

Figure 6:
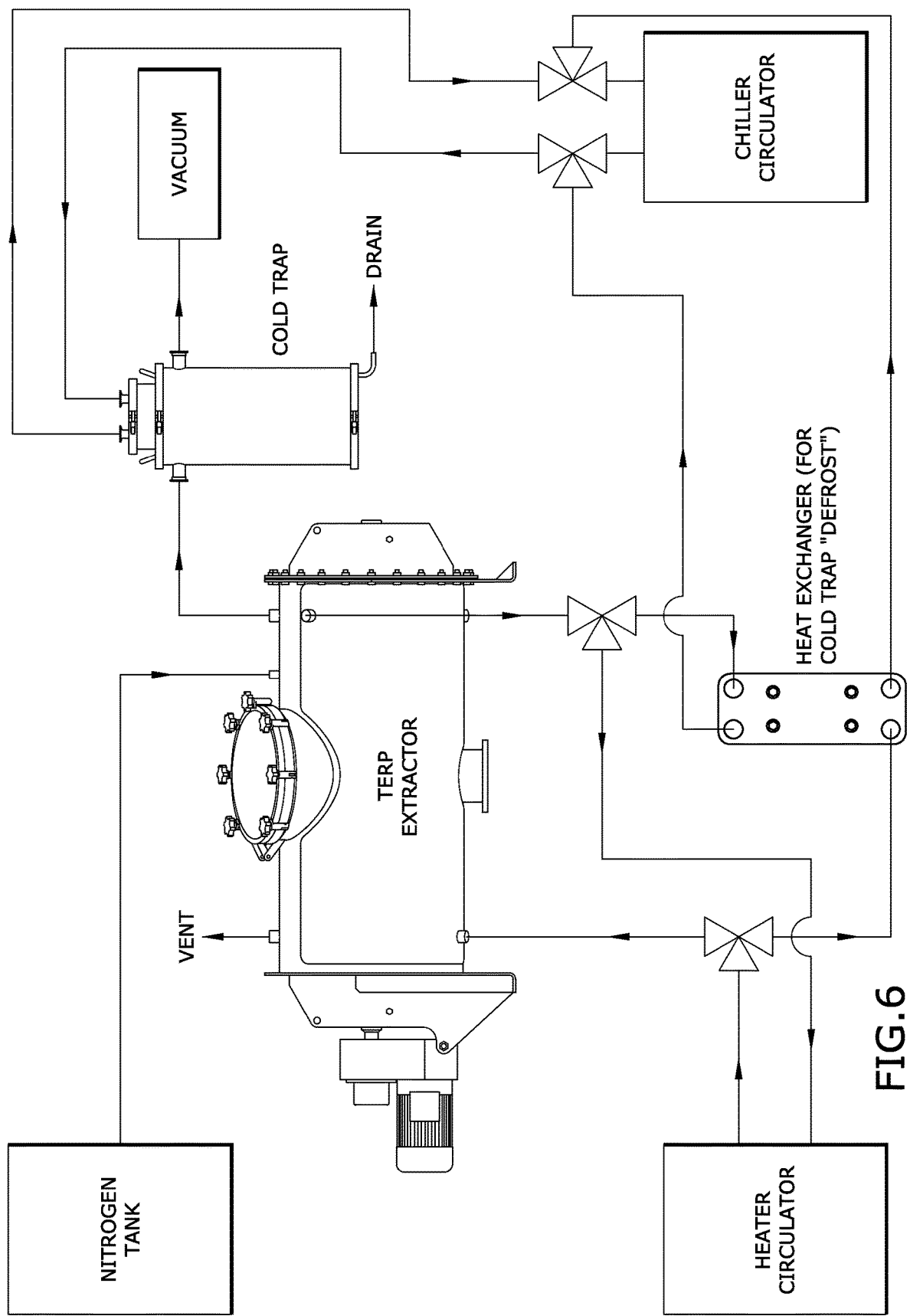
FIG. 6 is a schematic flow diagram of one embodiment of the present disclosure.

More specifically, and as shown in FIG. 6, the system may comprise an extractor with a dimple jacket encircling at least a portion thereof; a cold trap 56 operatively attached to the extractor, such that volatilized terpenes can travel from the extractor to the cold trap to condense/freeze to a surface of the cold trap during use thereof, wherein the cold trap 56 may hold a volume of a thermal fluid or dry ice; a circulating fluid chamber operatively attached to the cold trap 56, wherein fluid held within the circulating fluid chiller may comprise any suitable thermal transfer fluid; a heated fluid circulator operatively attached to the dimple jacket, wherein fluid held within the heated fluid circulator may comprise, for example, water or oil; a vacuum operatively attached to the extractor, such that the vacuum is capable of reducing pressure within the extractor; a heat exchanger 82 operatively attached to the heated fluid circulator and the chilled fluid circulator, whereby a heated fluid circuit is allowed to exchange with a chilled fluid circuit for rapidly defrosting frozen/condensed terpenes and other desirable volatile compounds contained within the cold trap 56; and a nitrogen tank operatively attached to the extractor.

Figure 1:
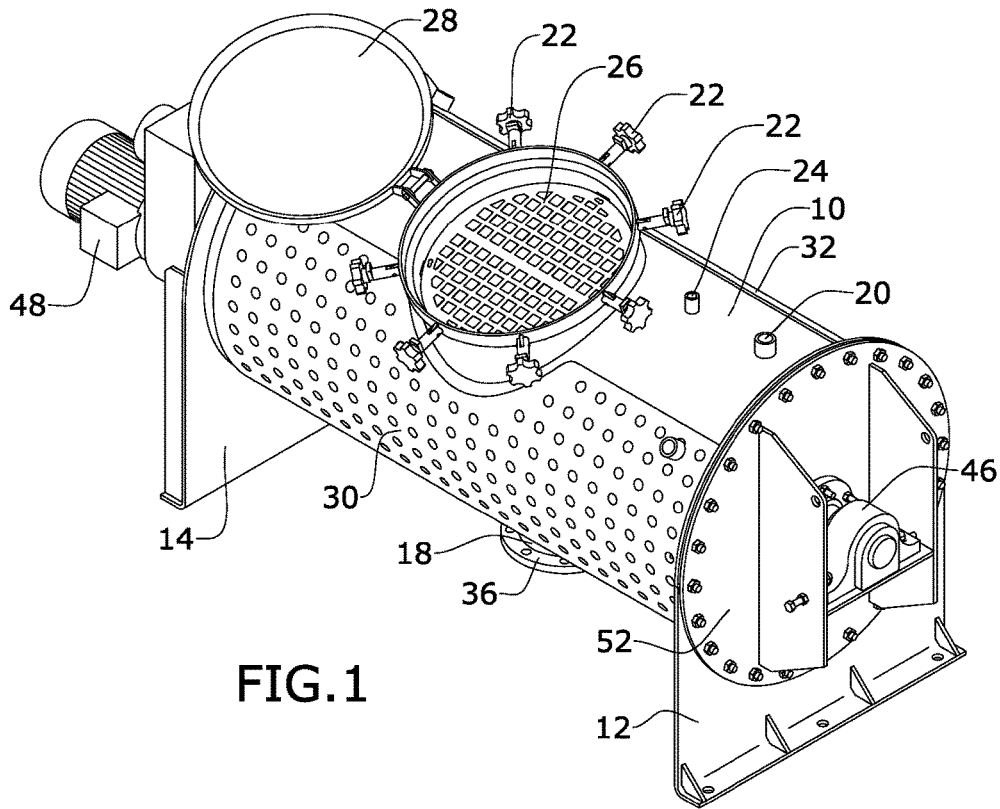
FIG. 1 is a perspective view of one embodiment of the present disclosure, shown with lid 28 open.
Figure 2:
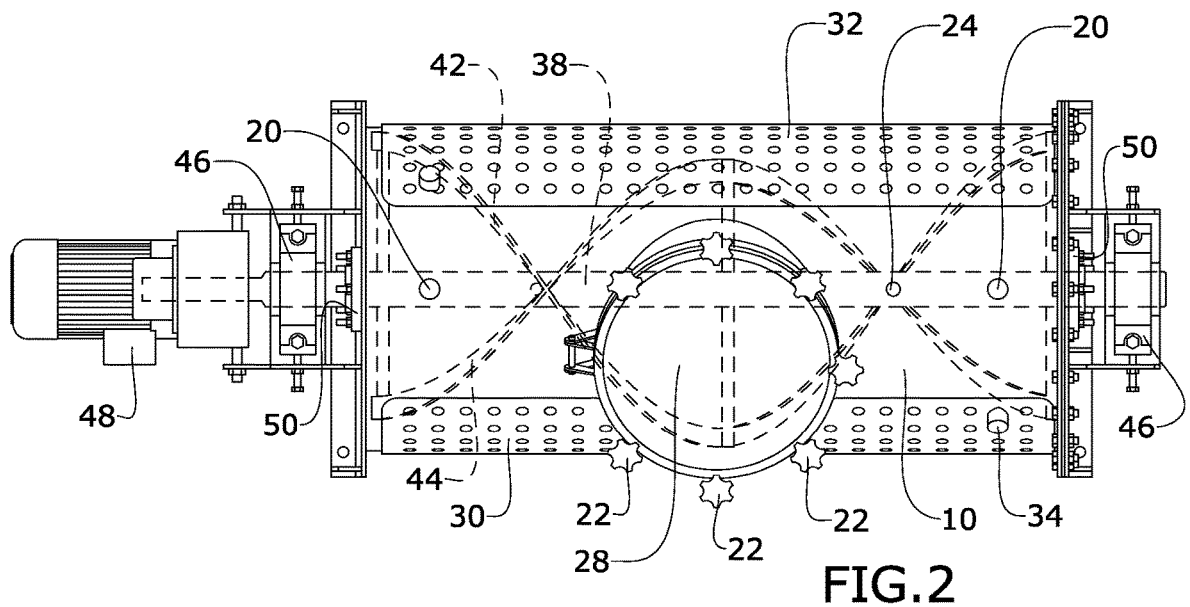
FIG. 2 is a top view of one embodiment of the present disclosure
Figure 3:
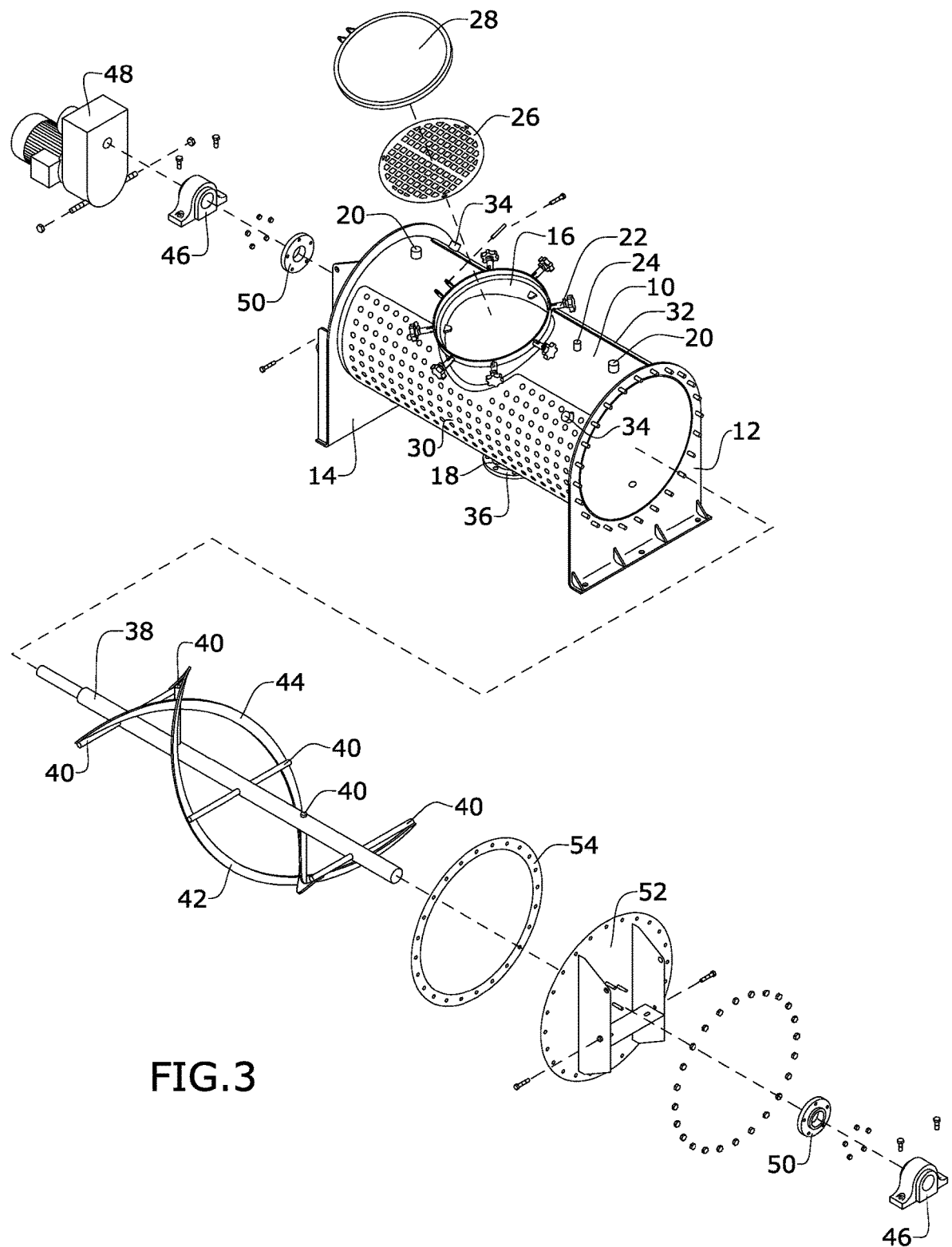
FIG. 3 is an exploded view of one embodiment of the present disclosure.

In embodiments, and as shown in FIGS. 1-3, the extractor may comprise an extractor body 10, wherein the extractor body 10 may comprise a horizontally oriented, substantially cylindrically shaped chamber with a motor endplate 14 closing off and supporting a first end thereof and an access endplate 12 closing off and supporting a second end thereof, such that the extractor body 10 is suspended between the motor endplate 14 and the access endplate 12. In embodiments, the access endplate 12 may be substantially arch-shaped with a circular access hole having a diameter approximately the same as a diameter of the end of the extractor body 10. An access plate 52 may be removably mounted to the access plate 52 to cover the access hole and, thus, to close off the end of the extractor body 10, wherein a gasket 54 may be positioned between the edge of the extractor body 10 and the access plate 52 to prevent leaks. As shown in FIG. 1, an exterior surface of the access plate 52 may include a bearing 46 attached thereto, wherein the agitator may be operatively attached to or engaged with the bearing 46. More specifically, as shown in FIG. 3, the access plate 52 may have an agitator orifice extending therethrough with a seal 50 attached to an outer surface of the access plate 52 surrounding the agitator orifice. The bearing 46 may be mounted to the access plate 52 over the seal 50.

The extractor body 10 may include at least two couplings 20 attached to an upper surface thereof, wherein a first of the two couplings 20 may be used as a vent, and a second of the two couplings 20 may be used to operatively attach the extractor to the cold trap 56. Similarly, a connector 24 on a top surface of the extractor body 10 may be used to operatively attach the extractor to the nitrogen tank.

As mentioned, the extractor body may include a dimple jacket encircling at least a portion of an outer surface thereof. The dimple jacket may comprise a front jacket 30 and a back jacket 32, together encircling at least a portion of the extractor body 10. The dimple jacket may include a pair of couplings 34 extending therefrom, wherein a first coupling of the pair of couplings 34 may be used to operatively attach the dimple jacket to the heat circulator, and a second coupling of the pair of coupling 34 may be used to operatively attach the dimple jacket to the heat exchanger.

The extractor body 10 may comprise a lower discharge manway 18 extending from a lower surface of the chamber, wherein the lower discharge manway 18 may comprise an opening with a tube 18 extending therefrom, wherein the tube 18 has a flange 36 attached to a distal end thereof, and a top loading manway 16 extending into a top surface of the chamber, wherein the top loading manway 16 comprises an opening with a wall extending upwards (i.e., away from an interior of the chamber) from outer edges of the opening, a grate 26 suspended within the top loading manway 16, and a lid 28 removably attached, such as hingeably attached, to the top loading manway 16. The extractor may further comprise at least one access lock 22 extending into the wall, such that the lid 28 may be secured in a locked configuration, as needed. When the lid 28 is open, a use may be able to access an interior of the extractor body.

The interior of the extractor body 10 may comprise an interior chamber with an agitator mounted therein. As shown in the Figures, the agitator may comprise a helix-shaped, such as a double helix shaped, agitator that extends lengthwise through the interior chamber of the extractor body. More specifically, and as shown in FIG. 3, the agitator may comprise a shaft 38, a first rigid ribbon 42 attached to the shaft 38 via a plurality of support bars 40 such that the first rigid ribbon 42 has a helix-like shape with respect to the shaft 38, and a second rigid ribbon 44 attached to the shaft 38 via a plurality of support bars 40 such that the second rigid ribbon 44 also has a helix-like shape with respect to the shaft 38, wherein the first rigid ribbon 42 and the second rigid ribbon 44 form a double-helix shape. A first end of the shaft 38 may be operatively attached to a motor 48 mounted to the motor endplate 14, and a second end of the shaft 38 may be mounted to a bearing 46 to the access endplate 52. As such, the agitator may extend within the interior chamber of the extractor body 10 from the motor endplate 14 to the access endplate 12. Additionally, when the motor 48 is actuated, the agitator may rotate within the internal chamber.

As shown in FIGS. 2 and 3, the motor 48 may be mounted to an exterior of the motor endplate 14, which may be substantially arch-shaped. A bearing 46 with a seal 50 may be mounted between the motor 48 and the motor endplate 14, wherein the bearing 46, seal 50, and motor 48 each include an opening sized to accommodate the first end of the shaft 38 therein. An agitator orifice may extend through the motor endplate 14 and align with the openings in the bearing 46, seal 50, and motor 58 such that the first end of the shaft 38 may extend through the motor endplate 14 into the motor 48.

Figure 4A:
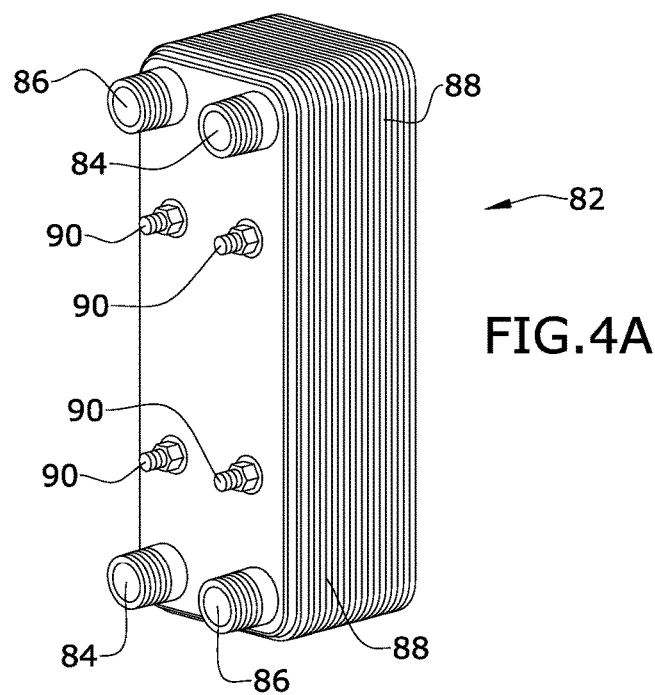
FIG. 4A is a perspective view of heat exchanger 82 from one embodiment of the present disclosure
Figure 4B:
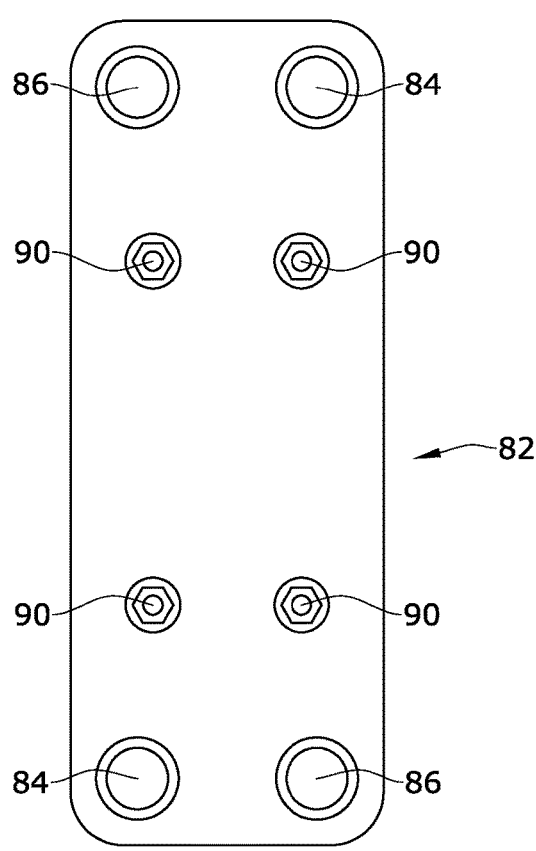
FIG. 4B is a front view of heat exchanger 82 from one embodiment of the present disclosure.
Figure 4C:
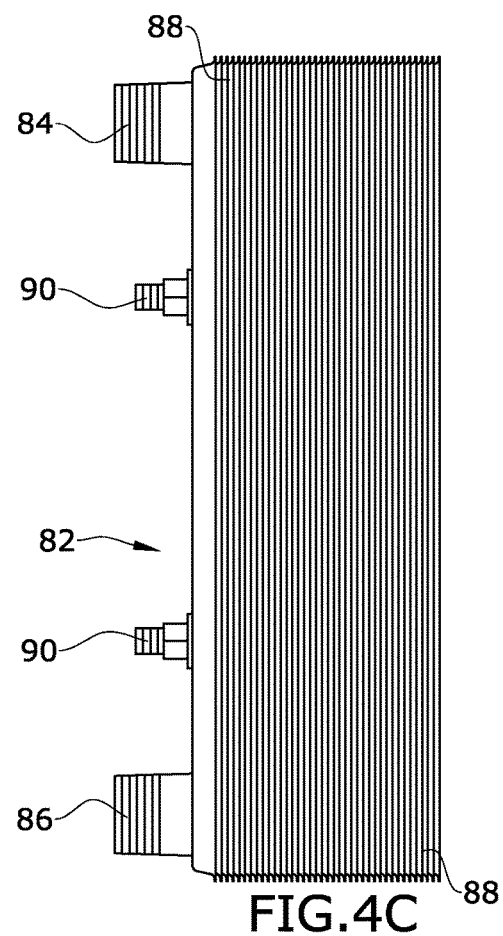
FIG. 4C is a right side view of heat exchanger 82 from one embodiment of the present disclosure.
Figure 5A:
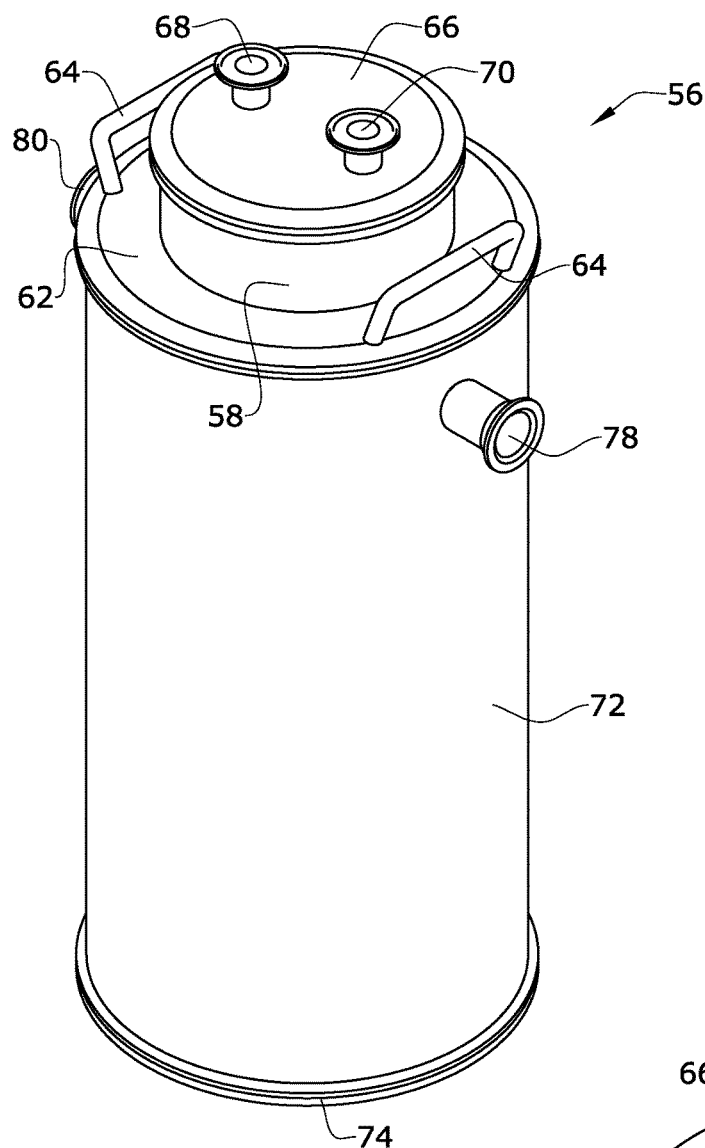
FIG. 5A is a perspective view of cold trap 56 from one embodiment of the present disclosure.
Figure 5E:
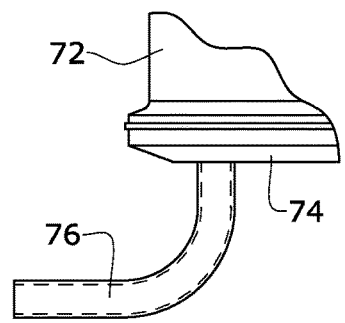
FIG. 5E is an enlarged detail view of a portion of cold trap 56 from one embodiment of the present disclosure.
Figure 5B:
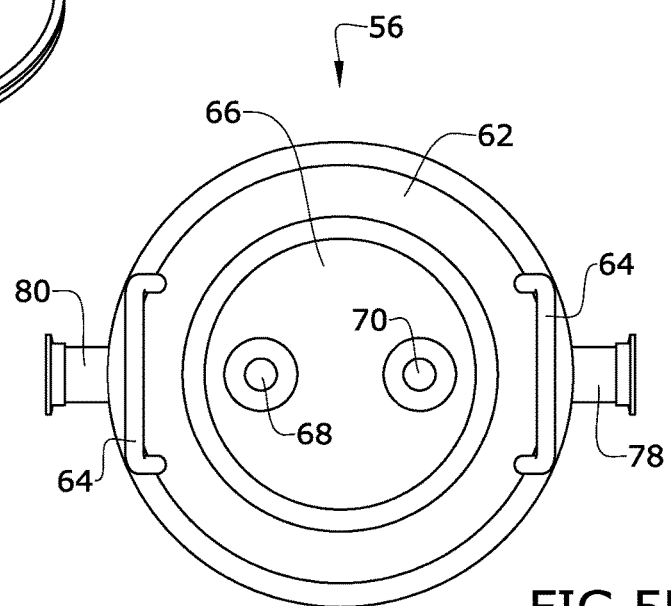
FIG. 5B is a top view of cold trap 56 from one embodiment of the present disclosure.

As shown in FIGS. 4A-4C, the heat exchanger 82 may comprise a conventional high efficiency heat exchanger, such as a plate heat exchanger. The heat exchanger 82 may include a plurality of cooling plates 88 stacked together, a pair of inlet connectors 84 and a pair of outlet connectors 86. The heat exchanger 82 may also comprise a plurality of mounting studs 90 to mount the heat exchanger 82 to the extractor body 10.

As shown in FIGS. 5A-5E, the cold trap 56 may comprise a substantially vertically oriented cylindrically shaped trap body 72 with an upper end cap 62 and a lower end cap 74. An inner spool body 58, which may be a substantially cylindrically shaped spool body with an inner spool bottom cap 60 and an inner spool top cap 66, may extend from an interior of the trap body 72 through the upper end cap 62. As such, an upper end of the inner spool body may extend upward from the upper end cap 62. A long spool 68, which may be a substantially cylindrical spool with a relatively small diameter, may extending from an interior of the inner spool body 58 through the inner spool top cap 66. As such, an upper end of the long spool 68 may extend upward from the inner spool top cap 66. A short spool 70 may also extend upward from the inner spool top cap 66. The short spool 70 may be operatively attached to an inlet on the chiller circulator, and the long spool 68 may be operatively attached to an outlet on the chiller circulator, such that fluid from the cold trap 56 may flow into the chiller circulator, and the output from the chiller circulator may flow into the cold trap 56.

In embodiments, the cold trap 56 may further comprise an inlet 78 attached to and extend into a side surface of the outer spool body 72 proximate to the upper end cap 62, wherein the inlet 78 allows the cold trap 56 to be operatively attached to the coupling 20 on the extractor. Similarly, an outlet 80 may be attached to and extend out of a surface of the outer spool body 72 proximate to the upper end cap 62, wherein the outlet 80 allows the cold trap 56 to be operatively attached to the vacuum pump. In embodiments, a drain 76 may extending outward from the lower end cap 74. Some embodiments of the cold trap 56 may also include a pair of handle 64 extending from, for example, the upper end cap 62.

Some embodiments of the system may further comprise loading and unloading manways that are open/closed using a pneumatic/hydraulic actuator system. Moreover, the operation of the system may be easily automated using a human machine interface program to control all system operations, such as valve control, heater control, chiller control, vacuum pump, agitator drive system, and the like.

The components of the system of the present disclosure may be made using any suitable materials. For example, in some embodiments, the extractor body 10 and internal agitator may be made of stainless steel. The motor and gearbox that drives the internal agitator may be equipment manufactured by, for example, Nord Drive Systems, wherein the rotation speed of the agitator may be controlled using an appropriate variable frequency drive. The cold trap 56 may also comprise stainless steel. The heat exchanger may be a conventional plate heat exchanger 82. The heated fluid circulator and the circulating fluid chiller may be equipment obtained from, for example, AEC Corp. and Across International, respectively. The vacuum pump may similarly be a conventional vacuum pump, such as a rotary vane or a dry scroll vacuum pump.

To use the system of the present disclosure, the extractor body 10 with the lower discharge manway full closed, may be loaded with cannabis or other desired plant material. After loading, the top loading manway 16 may be closed with the lid 28 and tightly sealed. A vacuum, such as at a pressure of about 29 in Hg, may be applied and maintained to the internal chamber of the extractor body 10. When the vacuum reduces the pressure within the extractor body 10, the boiling point of the terpenes contained within the plant material may be reduced, thus causing the terpenes to volatilize and reduce/eliminate reactive oxygen. The circulating chiller may be turned on and cooling fluid that is pumped to the cold trap 56 may be circulated and chilled to approximately $-80°$ C. The heated fluid circulator may be turned on, and the heated fluid may be circulated from the heated circulator to the dimple jacket on the extractor body 10, wherein the temperature of the heated fluid may be increased from an ambient temperature to approximately $100°$ C. The agitator within the extractor body 10 may then be turned on to agitate the cannabis material held within the interior chamber, thus exposing all portions of the cannabis material to the heated wall of the extractor body 10 during the extraction period, which may be from, for example, about 4 to about 24 hours. During the extraction period, the terpenes that are contained in the plant material may be volatilized from the vacuum and heat and may be pulled out of the extractor body 10 toward the cold trap 56, where they are collected and non-condensable gases are carried on to the vacuum pump. A stream of nitrogen gas may be optionally applied as a sweep gas to encourage terpenes to travel toward the cold trap, and the non-condensable nitrogen sweep gas may be varied onto and through the vacuum pump. This process may continue for about 4 to 24 hours.

At the end of the process, the heated fluid circulator temperature may be reduced to a temperature of, for example, about $50°$ C. and, once this temperature has been reached, a valve to the plate heat exchanger 82 may be opened, allowing fluid to circulate in parallel through the extractor body dimple jacket and the plate heat exchanger. A compressor on the circulating chiller may then be turned off, and the thermal fluid flowing from the circulating chiller and cold trap circuit may be opened up to the plate heat exchanger 82 in a counter current flow to the heat circuit also flowing through the plate heat exchanger 82, allowing the cold trap and the condensed/frozen terpenes to be defrosted and collected at the bottom of the cold trap 56. Terpenes may then be drained from the cold trap 56, and atmospheric pressure may be restored to the internal chamber of the extractor body 10. The lower discharge manway may be opened, and the internal agitator may escort the cannabis material out of the discharge port and into an appropriate discharge bin or discharge auger. The lower discharge manway may then be closed and fully sealed, and the process may be repeated for further batches of cannabis plant material.

When using the system of the present disclosure, cannabis terpenes are isolated in an oxygen free environment using a strong vacuum and gentle heat to extract the terpenes with low energy and reduced boiling points, leaving the cannabinoids in the plant material. Additionally, the input material remains dry, which improves downstream processing of retained cannabinoids. The vacuum distillation uses a low energy, oxygen free process that efficiently extracts very high quality cannabis terpenes without the use of solvents or high thermal energy steam. The output material has zero moisture content and is ideal for storage or downstream cannabinoid extraction.

Moreover, terpenes from freshly harvested plant material can also be extracted using the system of the present disclosure plus an added pre-condensation tube and shell heat exchanger chilled by a zero-degree fluid chiller. This allows the larger water load from fresh material to be condensed and segregated away from the terpenes, which continue down the vacuum pathway and are collected into the aforementioned cold trap. If available, vacuum bearings capable of holding ultra-high vacuum would allow for strong vacuum, and the system would require lower operating temperatures to achieve the same result. Using a vacuum pump rated for higher ultimate vacuum as well as adding a diffusion pump in line with the system vacuum pump would allow for a deeper ultimate vacuum and, therefore, reduce the necessary operative pressure to extract/isolate the terpenes present in the cannabis or other plant material.

While the above disclosure describes that the system and method of the present disclosure may be used to distill cannabis terpenes, it is not limited to such use. Rather, distilling terpenes from other plant material using the system and method of the present disclosure is also envisioned. Specifically, any plant material may be placed into the extractor body to efficiently extract or isolate high quality terpenes and other volatile aromatic compounds without the use of toxic solvents or high temperature steam.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

What is claimed is:

1. A system for vacuum distilling terpenes from plant material, the system comprising:
   an extractor comprising an extractor body with a lower discharge manway extending from a lower surface of the extractor body, a top loading manway extending from a top surface of the extractor body, an interior chamber with an agitator rotatable mounted within the interior chamber, and a dimple jacket encircling at least a portion of an exterior of the extractor body;

a cold trap operatively attached to the extractor body, such that volatilized terpenes travel from the extraction body to the cold trap to condense/freeze;

a circulating fluid chiller operatively attached to the cold trap;

a heated fluid circulator operatively attached to the dimple jacket;

a vacuum operatively attached to the extractor body, such that the vacuum is capable of reducing pressure within the extractor body; and a heat exchanger operatively attached to the heated fluid circulator, the circulating fluid chiller, and the extractor body.

2. The system of claim 1, wherein the extractor body comprises a horizontally oriented, cylindrically shaped chamber with a motor endplate closing off and supporting a first end thereof and an access endplate closing off and supporting a second end thereof, such that the extractor body is suspended between the motor endplate and the access endplate.

3. The system of claim 2, wherein:
the agitator comprises a double-helix shaped agitator with a central, elongate shaft; and
the shaft extends between and through each of the access endplate and the motor endplate.

4. The system of claim 3, wherein:
a motor is mounted to an exterior surface of the motor endplate;
the motor endplate includes a first shaft orifice extending therethrough, wherein the first shaft orifice is sized to accommodate insertion of a first end of the shaft therethrough, such that the first end of the shaft is operatively engaged with the motor; and a bearing is mounted to an exterior surface of the access endplate, wherein the access endplate includes a second shaft orifice extending therethrough, the second shaft orifice sized to accommodate insertion of a second end of the shaft therethrough, such that the second end of the shaft is operatively engaged with the bearing.

5. The system of claim 1, wherein the extractor further comprising a nitrogen tank operatively attached to the extractor body.

6. The system of claim 1, wherein the top loading manway includes a grate suspended therein and a lid configured to close off the top loading manway.

7. The system of claim 1, wherein the cold trap comprises a substantially vertically oriented cylindrically shaped trap body with an upper end cap and a lower end cap.

8. The system of claim 7, wherein the cold trap further comprises:
an inner spool body extending from an interior of the trap body through the upper end cap, the inner spool body comprising a substantially cylindrically shaped spool body with an inner spool bottom cap and an inner spool top cap;
a long spool extending from an interior of the inner spool body through the inner spool top cap, the long spool comprising a substantially cylindrical spool with a diameter smaller than a diameter of the inner spool body; and
a short spool extending upward from the inner spool top cap, wherein the short spool has a length shorter than the long spool.

9. The system of claim 8, wherein:
the short spool is operatively attached to an inlet on the circulating fluid chiller; and
the long spool is operatively attached to an outlet on the circulating fluid chiller.

10. The system of claim 7, wherein the cold trap further comprises a drain extending from the lower end cap.

* * * * *